United States Patent
Doth et al.

(10) Patent No.: US 6,482,648 B2
(45) Date of Patent: *Nov. 19, 2002

(54) STABLE TROPONIN PREPARATION AND THE USE THEREOF AS A CALIBRATOR/CONTROL IN IMMUNOASSAYS

(75) Inventors: Margit Doth, Krefeld (DE); Christoph Petry, Krefeld (DE)

(73) Assignee: Bayer Corporation, Tarrytown, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/950,240

(22) Filed: Oct. 14, 1997

(65) Prior Publication Data

US 2002/0012956 A1 Jan. 31, 2002

(30) Foreign Application Priority Data

Nov. 20, 1996 (DE) .......................... 196 47 927

(51) Int. Cl.⁷ .............................. G01N 33/53
(52) U.S. Cl. .................. 436/8; 435/7.1; 435/70.21; 435/240.27; 435/965; 435/967; 435/972; 436/518; 436/531; 436/811; 436/815; 436/15; 436/18; 436/11; 436/12; 436/13; 436/16; 436/17; 530/391.1; 530/391.5; 530/391.7; 530/807

(58) Field of Search ................ 435/7.1, 7.2, 7.93, 435/7.94, 7.95, 70.21, 240.27, 965, 967, 972; 436/518, 531, 8, 811, 815, 15, 18, 11, 12, 13, 16, 17; 530/391.1, 391.5, 391.7, 391.9, 807

(56) References Cited

U.S. PATENT DOCUMENTS 5,045,312 A  *  9/1991  Aston et al.
5,547,873 A  *  8/1996  Magneson et al.
5,583,200 A  * 12/1996  Larue et al.

FOREIGN PATENT DOCUMENTS

WO    WO 94/27156    * 11/1994

OTHER PUBLICATIONS

Ball et al., Biochemistry, 33:8464–8471, 1994.*
Stull et al., The Journal of Biological Chemistry. 252(3):851–857, 1977.*

* cited by examiner

*Primary Examiner*—Bao-Thuy L. Nguyen
(74) *Attorney, Agent, or Firm*—Andrew L. Klawitter; Jerome L. Jeffers

(57) ABSTRACT

The present invention relates to methods for the production of a stable troponin preparation and its use as a calibrator and/or control in immunoassays. The formulation is prepared from mammalian, preferably bovine, heart tissue which provides a calibrator/control composition which remains stable over a long period of time.

18 Claims, No Drawings

STABLE TROPONIN PREPARATION AND THE USE THEREOF AS A CALIBRATOR/CONTROL IN IMMUNOASSAYS

BACKGROUND OF THE INVENTION

Immunoassays are frequently used for the detection of proteins in serum or urine samples for medical/diagnostic purposes due to their particularly high specificity and sensitivity. For such immunoassays not only are one or two specific antibodies required but there is also needed a calibrator which is used as a reference standard for quantifying the patient samples. The storage of the calibrators for several months to two years at 4° C. is sometimes necessary for automated assays in large analytical laboratories. Depending on the analyte in question, these demands on the stability of the calibrator formulation can present problems, if for example, its solubility under physiological salt and pH conditions is not guaranteed. Examples which may be mentioned in this regard are troponin I and troponin T, which are only sufficiently stable and soluble in denaturing solutions (6 M urea, 0.01 M of dithiothreitol). It is however not possible to carry out an immunoassay using this denaturing formulation since denaturing conditions would affect the antibodies by modifying their secondary structure, so that they could not bind the troponin analyte. Other factors in the case of Troponin could be its tendency to stick to surfaces such as glass as well as possible chemical instability thereby complicating the preparation of stable calibrators.

It is known that proteins are relatively unstable in solution and that reagents containing them are frequently sold in lyophilised form together with a solvent of a suitable composition in which they are dissolved prior to their application by the user. If the solutions obtained in this manner are stored at 4° C. they can be used for several days even if a certain change in the concentration of the reagent is observed in the daily detection process. Thus, if the reference solutions obtained from the lyophilised material are to be stored over longer periods they are generally frozen in a standard dosage form as is recommended in the case of troponin I and troponin T.

SUMMARY OF THE INVENTION

The present invention relates to a calibrator with very high stability at 4° C. and higher temperatures for use in immunoassays. The calibrator material comprises a carefully produced preparation of cardiac muscle in which troponin is retained in its native form.

The cardiac muscle preparation can also be used as a control which can be integrated into a laboratory's quality control scheme. Controls are not different from calibrators in the way they are made with the possible exception that their stability requirements are less stringent. There is, however, a difference in how they are used since calibrators are used to set up an assay while controls are run on a daily basis to ensure that the assay continues to perform adequately. The following description emphasizes the use of the heart muscle homogenate as a calibrator, but it is to be understood that the description is also applicable for the preparation of heart muscle, homogenates which are to be used as controls.

DESCRIPTION OF THE INVENTION

Standard methods for isolating and purifying troponin use organic solvents and/or high salt concentrations. While the examples herein involve troponin I, the procedures disclosed are equally applicable to tropinin C and T as well as several other molecules present in heart tissue which are indicators of cardiac muscle damage.

The new method consists in homogeneously comminuting fresh mammalian cardiac muscle, which can be stored in a frozen state with a physiological buffer solution. Human or bovine heart tissue is preferred. Other mammalian heart tissue can also be used provided that it contains amino acid sequences which are similar to those present in the human and bovine material. Suitable homogenising media are buffer solutions with pH values in the neutral, weakly acidic or weakly alkaline range preferably about (pH 5.5 to 8.5), such as for example PBS (dipotassium hydrogen phosphate/sodium dihydrogen phosphate), TRIS (tris[hydroxymethyl] amino-methane), imidazole, MES (2-[N-morpholino] ethane-sulphonic acid] and HEPES (N-[2-hydroxyethyl]-piperazine-N'-[2-ethanesulphonic acid]) containing a salt to keep the ionic strength in the physiological range in order to maintain the molecules in their natural configuration. The salt concentra-tions are within the physiological concentration range, such as for example 10 to 880 mM NaCl, $MgCl_2$, KCL or $CaCl_2$. Detergents such as Triton X 100 or Tween 20; protease inhibitors such as trypsin inhibitor, phenylmethyl sulphonyl fluoride (PBSF), leupeptin and/or pepstatin, and antioxidants such as DTT or $\beta$-mercaptoethanol are preferably used as additives. Detergents generally prevent the calibrator materials from sticking to glass and plastic surfaces, whereas antioxidants help to maintain the analyte in the monomeric state by inhibiting di-sulfide bridge formation. Protease inhibitors prevent degradation of the troponin molecule by non-specific proteases present in the tissue extract.

The homogenate is centrifuged off and is preferably stored at a temperature of from −20° C. to −80° C. since low temperatures stabilize protein solutions upon storage. Dilutions of this preparation display reactivity with the antibodies used in the immunoassay which are specific for cardial troponin and in particular troponin I. In preparing calibrators, the heart homogenate, which is typically bovine heart tissue, is diluted in a dilution matrix. The troponin I activity in the above mentioned cardiac muscle preparation was not found to be present in a similarly processed skeletal muscle preparation. It was also found that it is only in the cardiac muscle preparation that the aforementioned antibodies recognize a protein which displays the same run properties in denaturing gel electrophoresis as isolated cardial troponin I.

The above mentioned preparation is also stable for several days in various physiological buffers at 20° C. and at 4° C. Suitable dilution matrices are processed and unprocessed human or animal sera or plasmas or the buffers mentioned as isolation media. In addition, preservatives such as sodium azide and Proclin 150 and stabilized proteins such as bovine serum albumin (BSA) or gamma globulins are used. Diluting the heart homogenate into a 6% aqueous BSA solution with the various additives mentioned is a preferred method for preparing the calibrator matrix. Typically, calibrators for immunoassays are prepared by dissolving the analyte to be measured in normal human serum. This is done to ensure that the calibrators match the clinical serum sample as closely as possible. However, the heart homogenate of the present invention is not very stable when incorporated into normal human serum. Therefore, an artificial matrix of normal human serum is prepared using BSA or other protein such as human serum albumin, fetal calf serum, bovine gamma globulin or oval bumin in an amount sufficient to approximate the average protein concentration of human serum (6% in the case of BSA) in combination with stabilizers along with buffer and salts to approximate the ionic strength of serum. For the purpose of improved reproducibility, the above mentioned preparation can also include the following steps: fractionation by routine methods such as for example gel filtration, the high-speed removal by centrifugation of insoluble components and/or filtration through sterile filters. In this manner it is possible to prepare stable liquid calibrators for the above mentioned immunoassay for the diagnosis of cardiac infarction in a very simple, inexpensive way. Furthermore the troponin preparation contains the molecule to be detected in a form in which it is predominately found in patient samples. The troponin in healthy heart muscle exists as a complex of troponin I, T and C and it is believed that in the heart homogenate of the present invention, troponin is present in the natural ITC complex form. Accordingly, the method of this invention can be used to prepare calibrators for the T and C forms of troponin as well as the I form. It therefore provides a more authentic control for a diagnostic test than a formulation containing isolated troponin I, T or C. Since troponin is present in the form of a complex in its native form and this complex represents the more stable form, the above mentioned bovine cardiac muscle homogenate can be treated with crosslinkers in order to obtain a covalent bond between the three components of the complex. This bond is more stable than the naturally occurring molecular interactions within the troponin complex since the covalent bond between the parts of the complex introduced by the crosslinkers prevent the complex from breaking up. Suitable crosslinkers are homobifunctional molecules such as for example 1-ethyl-3-3[dimethylaminopropyl] carbodiimide hydrochloride (EDC), (bis[sulphosuccinimidyl]-suberate ($BS^3$) or sulphodisuccinimidyl tartrate (sulpho-DST). Formation of the troponin crosslinker complex is desirable when increased stability of the calibrator is desired. While the uncrosslinked material shows very good stability, some commercial assays require stability for a year or more in which case crosslinking would be beneficial. The present invention is further illustrated by the following examples.

EXAMPLE 1

Shock-frozen bovine cardiac muscle, 31 g, was homogenized with 30 ml of a cooled homogenisation buffer (1.39 g/l $K_2HPO_4$, pH 7.3, 8.77 g/l NaCl, 0.312 g/l $Na(HPO_4)_2$*2 $H_2O$, 0.1% Tween 20, 0.1 mM dithiothreitol). The homogenate was centrifuged off at 1000 g for 20 minutes, aliquoted and frozen. Typically, calibrators for immunoassays are prepared by dissolving the analyte to be measured in normal human serum. This is done to ensure that the calibrators match the clinical serum sample as closely as possible. However, the heart homogenate of the present invention is not very stable when incorporated into normal human serum. In various matrices, dilutions of this homogenate displayed the following stability values (Table 1). The stability was determined by comparing the diluted homogenate with similarly prepared dilutions of pure troponin ITC complex obtained from a commercial source whose effective troponin I content had been measured by a standard method. The pure ITC complex was used to prepare gravimetrically a research lot of calibrators. This reference lot of calibrators (stored at −80° C.) was used with experimental troponin I (from the bovine heart homogenate) assay reagents to construct a standard curve to measure troponin I concentrations. The bovine heart homogenate based calibrators were stressed under various conditions and measured as unknown samples versus the reference lot calibrators to detect any fall off in activity. The preparation was analysed in a Bayer Immuno 1™ analyser (Bayer Diagnostics). The assay form was a sandwich using the following antibodies: 1) a polyclonal goat antibody which had been affinity-purified using a peptide from the sequence of human cardial troponin I, 2) a monoclonal antibody against human cardial troponin I. The first antibody of the sandwich is labeled with FITC and is immobilised on magnetic particles by means of anti-FITC. The second antibody of the sandwich contains alkaline phosphatase and catalyses a color forming reaction by means of which the quantity of antigen is determined. This analyzer reports experimental results in terms of AU, i.e. (optical) absorbance units/min. before the results are translated into clinical units. The amino acid sequences of human and bovine cardial troponin I are very similar, which explains the antibody cross-reactivity. Bovine cardiac muscle can therefore be used for the calibrator preparation. In principle human and other mammalian tissue can also be used for the preparation. Referring to Table 1, the term calibrator buffer refers to a preparation of the bovine cardiac muscle in:

6.81 g/L imidazole 5.84 g/L sodium chloride 0.9 g/L sodium azide 2.0 g/L Triton X100

1 ml/L Proclin 150

60 g/L BSA and unprocessed serum refers to serum which had not been lipidized or treated with organic solvents.

Referring to the data presented in Table 1, there is no significant difference between the stability data of the homogenate in buffer or in serum. In fact, in longer lasting studies the buffer proved to be superior over all to serum matrices. The data presented in the table have a certain scatter which can be expected in studies running over a period of several weeks.

EXAMPLE 2

A cardiac muscle homogenate was prepared as described in Example 1. The total protein concentration was adjusted to 2 mg/ml and quantities in the range from a 2.5 to 250-fold molar excess versus the apparent troponin I concentration of the following crosslinkers were added: 1-ethyl-3-3[di-methylamino-propyl]carbodiimide hydrochloride (EDC), (bis[sulphosuccinimidyl]) suberate ($BS^3$) or sulpho disuccinimidyl tartrate (sulpho-DST). The reaction time at room temperature was 3 hours. Then the preparations were diluted further and analyzed as described under Example 1.

| sample | dilution | matrix | 0 | 1 | 4 | 7 | 14 | 21 | 28 | 42 | 49 |
|---|---|---|---|---|---|---|---|---|---|---|---|
| | | | \multicolumn{9}{c}{storage time at 4° C. (in days)} | | | | | | | | | |
| bovine cardiac | 1:100 | calibrator- | 2.2443 | 2.1913 | 2.149 | 2.135 | 2.1714 | 2.1614 | 2.1428 | 2.0826 | 2.0856 |
| muscle preparation | 1:1000 | buffer | 0.1516 | 0.1434 | 0.1353 | 0.1279 | 0.1227 | 0.1306 | 0.1319 | 0.1257 | 0.1296 |
| | 1:100 | unprocessed | 1.7778 | 1.7283 | 1.7261 | 1.6484 | 1.7363 | 1.7163 | 1.7643 | 1.7327 | 1.732 |
| | 1:1000 | human serum | 0.0811 | 0.0849 | 0.0987 | 0.1009 | 0.1105 | 0.1152 | 0.123 | 0.1214 | 0.1192 |
| | | | \multicolumn{9}{c}{storage 20° C. (in days)} | | | | | | | | | |
| bovine cardiac | 1:100 | calibrator- | 2.2443 | 2.1465 | 2.2201 | 2.1878 | 2.1554 | 2.1841 | 2.2295 | 2.1609 | 2.1381 |
| muscle preparation | 1:1000 | buffer | 0.1516 | 0.1469 | 0.1561 | 0.164 | 0.1705 | 0.1741 | 0.1787 | 0.1757 | 0.1749 |

-continued

| sample | dilution | matrix | 0 | 1 | 4 | 7 | 14 | 21 | 28 | 42 | 49 |
|---|---|---|---|---|---|---|---|---|---|---|---|
| | 1:100 | unprocessed | 1.7778 | 1.735 | 1.6958 | 1.7274 | 1.7734 | 1.7467 | 1.7909 | 1.6449 | 1.6351 |
| | 1:1000 | human serum | 0.0811 | 0.0795 | 0.0824 | 0.0836 | 0.093 | 0.0997 | 0.1017 | 0.0983 | 0.0976 |

The values represent AU/min

What is claimed is:

1. Stable calibrator/control formulation for immunoassays of indicators of cardiac muscle damage, characterized in that it comprises the supernatant of a centrifuged homogenate of crude extracts of mammalian cardiac muscle in a dilution matrix containing buffer and salt to approximate the ionic strength of human serum.

2. Stable calibrator/control formulation of claim 1 wherein the formulation also contains protein in an amount sufficient to approximate the protein concentration of human serum.

3. Stable calibrator/control formulation of claim 2 wherein the protein is bovine serum albumin.

4. Stable calibrator/control formulation of claim 1 having a pH of from about 5.5 to 8.

5. Stable calibrator/control formulation of claim 1 containing a detergent, a protease inhibitor and an antioxidant.

6. The calibrator/control formulation of claim 1 wherein the indicator of cardiac damage is troponin.

7. The calibrator/control formulation of claim 6 wherein the troponin is Troponin I.

8. The calibrator/control of claim 1 which has been filtered after centrifugation.

9. A stable calibrator for immunoassays for troponin as an indicator of cardiac muscle damage which comprises the supernatant of a centrifuged homogenate of crude extracts of mammalian cardiac muscle in a dilution matrix buffered to a pH of from about 5.5 to 8.0, a salt to approximate the ionic strength of human serum and protein in an amount sufficient to approximate the protein concentration of human serum.

10. The calibrator of claim 9 which contains a detergent, a protease inhibitor and an antioxidant.

11. The calibrator of claim 9 wherein the troponin is Troponin I.

12. The calibrator of claim 9 wherein the mammalian cardiac muscle is bovine cardiac muscle.

13. A method of calibrating an immunoassay for troponin which method comprises comparing the assay result with the calibrator of claim 9 which contains a known amount of troponin.

14. The stable calibrator of claim 9 which has been filtered after centrifugation.

15. A stable calibrator for immunoassays for Troponin I as an indicator of cardiac muscle damage which comprises the supernatant of a centrifuged homogenate of crude bovine cardiac muscle in a dilution matrix buffered to a pH of from about 5.5 to 8.0, a salt to approximate the ionic strength of human serum and bovine serum albumin in an amount sufficient to approximate the protein concentration.

16. The stable calibrator of claim 15 which also contains a detergent, a protease inhibitor and an antioxidant.

17. A method of calibrating an immunoassay for Troponin I which method comprises comparing the assay result with the calibrator of claim 15 which contains a known amount of Troponin I.

18. The stable calibrator of claim 15 which has been filtered after centrifugation.

\* \* \* \* \*